(12) United States Patent
Nishino et al.

(10) Patent No.: US 8,196,450 B2
(45) Date of Patent: Jun. 12, 2012

(54) GAS CHROMATOGRAPH

(75) Inventors: Masanori Nishino, Kyoto (JP);
Takahiro Nishimoto, Kyoto (JP);
Masaki Kanai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 632 days.

(21) Appl. No.: 12/439,159

(22) PCT Filed: Aug. 28, 2006

(86) PCT No.: PCT/JP2006/316879
§ 371 (c)(1),
(2), (4) Date: Feb. 26, 2009

(87) PCT Pub. No.: WO2008/026241
PCT Pub. Date: Mar. 6, 2008

(65) Prior Publication Data
US 2009/0255322 A1  Oct. 15, 2009

(51) Int. Cl.
*G01N 1/00* (2006.01)
(52) U.S. Cl. ..................... 73/23.41
(58) Field of Classification Search ............. None
See application file for complete search history.

(56) References Cited

U.S. PATENT DOCUMENTS 5,313,832 A * 5/1994 Stephan et al. ............ 73/204.26
5,534,998 A * 7/1996 Eastgate et al. ............. 356/316

FOREIGN PATENT DOCUMENTS

| JP | 52-40195 U | 3/1977 |
|---|---|---|
| JP | 58-182156 U | 12/1983 |
| JP | 59-120956 A | 7/1984 |
| JP | 6-94691 A | 4/1994 |
| JP | 9-43215 A | 2/1997 |
| JP | 11-51920 A | 2/1999 |
| JP | 2001-235458 A | 8/2001 |

OTHER PUBLICATIONS

International Search Report for the Application No. PCT/JP2006/316879 mailed Sep. 26, 2006.

(Continued)

*Primary Examiner* — Peter Macchiarolo
*Assistant Examiner* — Alex Devito
(74) *Attorney, Agent, or Firm* — Cheng Law Group, PLLC

(57) ABSTRACT

A sample vaporization unit that attains enhancing of reproducibility through fixing of the sample vaporization unit. Sample vaporization unit (4) at its one end is connected to the distal end of glass insert (2) and at its other end is connected via glass tube (5) to one end of capillary column (6). The other end of the capillary column (6) is led to detector (8). The sample vaporization unit (4) is comprised of base frame (22), flow channel (24) provided in the base frame (22), and rugged portion (26) for sample vaporization provided by microfabrication within the flow channel (24). Any liquid sample flowing through the flow channel (24) is vaporized by feeding of energy to the rugged portion (26), and the vapor is subjected to separation by means of the column (6) and detection by means of the detector (8).

16 Claims, 7 Drawing Sheets

OTHER PUBLICATIONS

Lehmann, V. "Porous Silicon—A New Material for MEMS", The 9th Annual International Workshop on Micro Electro Mechanical Systems, 1996, pp. 1-6.

Hynes, A. M. et al., "Recent Advances in Silicon Etching for MEMS Using the ASE Process", Sensors and Actuators, 1999, vol. 74, pp. 13-17.

Silicon Micromachining, 2001, pp. 323-328.

Recent Trends in Microfabrication Studies, 2000, vol. 6, pp. 14-20.

Jansen, Henri et al., "The Black Silicon Method: A Universal Method for Determining the Parameter Setting of a Fluorine-Based Reactive Ion Etcher in Deep Silicon Trench Etching with Profile Control", J. Micromech. Microeng., 1995, vol. 5, pp. 115-120.

Kruse, Rebecca A. et al., "Experimental Factors Controlling Analyte Ion Generation in Laser Desorption/Ionization Mass Spectrometry on Porous Silicon", Anal. Chem., 2001, vol. 73, pp. 3639-3645.

* cited by examiner

GAS CHROMATOGRAPH

TECHNICAL FIELD

The present invention relates to a gas chromatograph in which a liquid sample is vaporized by a sample vaporization unit and is then separated into its components to detect the sample components.

BACKGROUND ART

FIG. 7 is a schematic view of a conventional gas chromatograph. Reference numeral 2 denotes a glass insert of a sample introduction unit, and the distal end of the glass insert 2 is connected to one end of a capillary column 6. The other end of the capillary column 6 is connected to a detector 8. A carrier gas introduction tube 10 is connected to the proximal end portion of the sample introduction unit to supply a carrier gas whose pressure has been regulated.

A septum purge flow channel 12 for discharging part of a carrier gas is also provided at the proximal end portion of the sample introduction unit. The proximal end portion of the sample introduction unit is sealed with a septum 14. A needle extending from a sample injector is allowed to penetrate the septum 14 in such a manner that the distal end of the needle is inserted into the inside of the glass insert 2, and then a liquid sample is injected into the glass insert 2.

The outer circumferential portion of the glass insert 2 is covered with a heating block 51, and glass wool 53 held by a graphite ferrule 55 is placed inside the glass insert 2. A liquid sample is injected from the upper side of the glass insert 2 into the glass insert 2 through a needle. The liquid sample is allowed to flow downward together with a carrier gas, and is then brought into contact with the glass wool 53. The glass wool 53 is previously heated to about 250° C. by the heating block 51, and therefore the liquid sample flowing through the glass wool is heated as well as mixed and is then vaporized. The vaporized sample is split into two and introduced into both the capillary column 6 and a split flow channel 11. The sample flowing through the capillary column 6 is separated into its components, and the sample components are detected by the detector 8.

Non-Patent Document 1: Anal. Chem. 73, 3639-3645 (2001)
Non-Patent Document 2: V. Lehmann, The 9th Annual International Workshop on Micro Electro Mechanical Systems, 1-6 (1996)
Non-Patent Document 3: Sensors and Actuators 74, 13-17, (1999)
Non-Patent Document 4: Silicon Micromachining (by M. Elwenspoek and H. V. Jansen), p. 323-326, 2001
Non-Patent Document 5: Henri Jansen et al., J. Micromech. Microeng. 5, 115 (1995)
Non-Patent Document 6: "Recent Trends in Microfabrication Studies" vol. 6, p. 14-20, 2000

DISCLOSURE OF THE INVENTION

Problem(s) to be Solved by the Invention

In the case of such a conventional gas chromatograph, the glass wool 55 placed in a vaporization chamber cannot be directly heated. Therefore, there is a case where a sample is not instantly vaporized in the vaporization chamber, thereby affecting the reproducibility of analysis.

Further, since the glass wool cannot be washed, it is necessary to exchange it, but there is a case where the size of the glass wool is changed before and after exchanging. In such a case, it is difficult to keep the glass wool at the same position in the glass insert 2 even when the ferrule is used, thereby affecting measurement reproducibility. In addition, the position of the glass wool in the glass insert is changed when the pressure of a carrier gas is changed. This also affects reproducibility of measurements.

It is therefore an object of the present invention to provide a gas chromatograph in which a sample vaporization unit is fixed to be capable of improving reproducibility.

The present invention is directed to a gas chromatograph including: a sample vaporization unit having a base frame, a flow channel provided in the base frame, and a rugged portion provided by microfabrication in the flow channel to vaporize a sample; an energy supply unit for supplying energy for heating the rugged portion; a column connected to the sample vaporization unit to separate the sample carried by a carrier gas from the sample vaporization unit into its components; and a detector connected to the discharge side of the column to detect the components of the sample discharged from the column.

The material of the rugged portion is not particularly limited as long as it can absorb energy. For example, the rugged portion is made of a material selected from the group consisting of silicon, an inorganic silicon compound, metal, carbon, ceramic, and a complex of two or more of them.

A preferred example of the rugged portion is one made of porous silicon. The porous silicon can be formed by, for example, anodizing silicon in hydrofluoric acid.

Another preferred example of the rugged portion is a pattern formed on the surface of a substrate so as to have a rectangular cross section. Such a pattern having a rectangular cross section can be formed by, for example, deep ion etching of silicon.

Yet another preferred example of the rugged portion is one constituted from needle-shaped projections. The needle-shaped projections can be formed by, for example, anisotropic dry etching of silicon. One example of such a rugged portion constituted from needle-shaped projections is black silicon.

Yet another preferred example of the rugged portion is one formed by molding. The rugged portion formed by molding may have a rectangular cross section or a circular cross section or may be constituted from needle-shaped projections. Such a rugged portion having a rectangular cross section or a circular cross section or constituted from needle-shaped projections may be formed by injection molding.

One example of the energy supply unit is one having an electrode connected to the rugged portion and a power supply device for supplying an electric current to the rugged portion through the electrode. In this case, the electrode for connecting the rugged portion to the power supply device may be formed by sputtering or vapor deposition.

Another example of the energy supply unit is an energy source for supplying radiant energy to the rugged portion. An example of the energy source includes an induction heater (IH). In this case, it is possible to irradiate the rugged portion with energy emitted from a position far from the rugged portion.

Between the energy source and the rugged portion, a lens for converging energy emitted from the energy source may be provided to efficiently irradiate the rugged portion with the energy. The lens is preferably one capable of converging energy. In a case where the energy is light, a converging lens may be used.

The base frame constituting the sample vaporization unit may be formed by bonding together at least two substrates. In this case, the flow channel is formed on at least one of the substrates.

Further, in this case, it is preferred that one of the substrates is a silicon substrate and the other substrate is a glass substrate.

Effect of the Invention

As described above, since the gas chromatograph according to the present invention includes a sample vaporization unit having a base frame, a flow channel provided in the base frame, and a rugged portion provided by microfabrication in the flow channel to vaporize a sample and an energy supply unit for supplying energy for heating the rugged portion, it is not necessary to provide glass wool, a glass insert, and a ferrule for holding the glass wool. This saves users from having to replace glass wool, a glass insert, and a ferrule, thereby making it possible to attain reproducibility of measurements and to reduce the size of the gas chromatograph.

When the energy supply unit has a power supply device, an electric current can be applied to porous silicon to increase the temperature of the porous silicon. This makes it possible to instantly vaporize a sample.

When the energy supply unit is a heat source for irradiating the rugged portion with radiant heat, the rugged portion can be irradiated with energy emitted from a position far from the rugged portion to increase the temperature of porous silicon.

Figure 1:
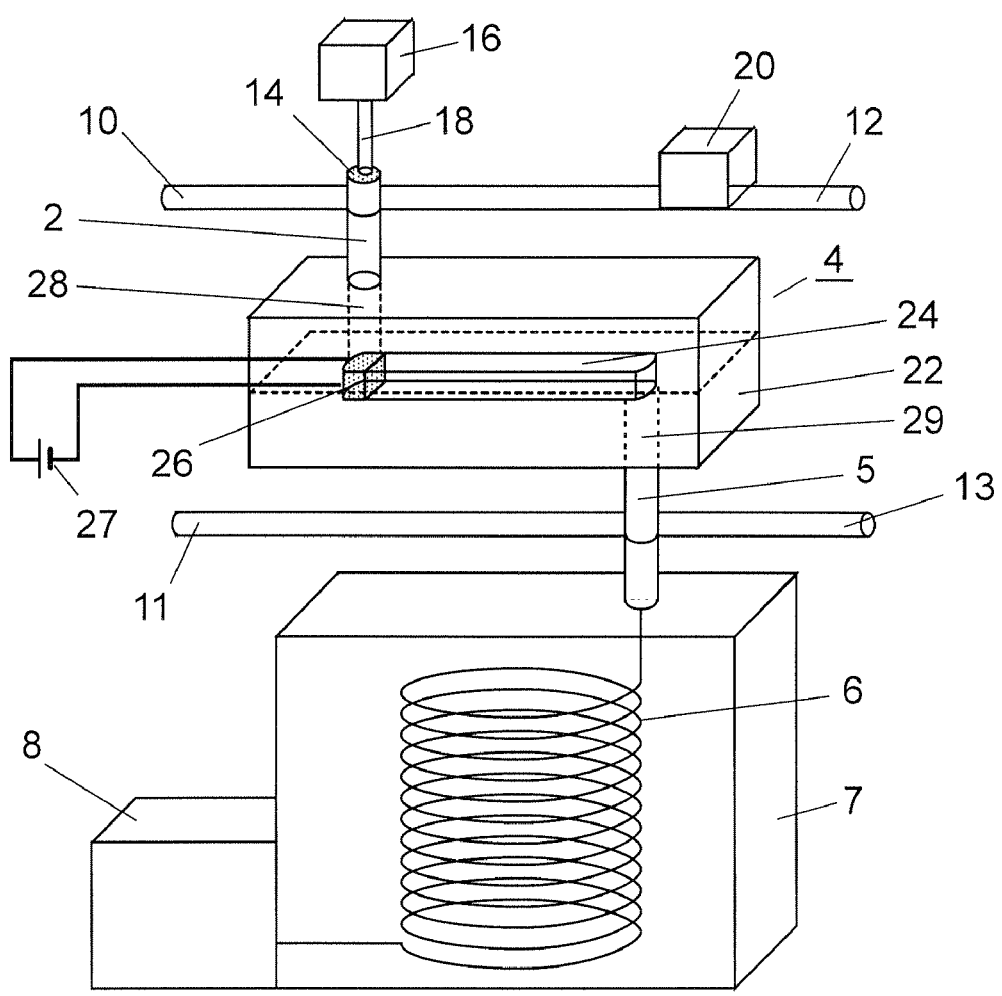
FIG. 1 is a schematic perspective view of a gas chromatograph according to a first embodiment of the present invention.

DESCRIPTION OF THE REFERENCE NUMERALS 2. glass insert
4. sample vaporization unit
5. glass tube
6. capillary column
7. oven
8. detector
10. 11. carrier gas flow channel
12. septum purge flow channel
13. split flow channel
14. septum
16. sample injector
18. needle
22. substrate
24. flow channel
26. rugged portion
27. power supply device

DETAILED DESCRIPTION OF THE INVENTION

Hereinbelow, a first embodiment of the present invention will be described with reference to the accompanying drawings.

FIG. 1 is a schematic perspective view of a gas chromatograph according to the first embodiment of the present invention. Reference numeral 2 denotes a glass insert of a sample introduction unit, and the distal end of the glass insert 2 is connected to one end of a sample vaporization unit 4. The other end of the sample vaporization unit 4 is connected to one end of a capillary column 6 through a glass tube 5, and the other end of the capillary column 6 is connected to a detector 8. The capillary column 6 is placed in an oven 7 for maintaining the capillary column 6 at a constant temperature.

A carrier gas introduction tube 10 is connected to the proximal end portion of the sample introduction unit to supply a carrier gas whose pressure has been regulated by a pressure-regulating system (not shown) to the proximal end portion of the sample introduction unit.

A septum purge flow channel 12 for discharging part of a carrier gas is also provided at the proximal end portion of the sample introduction unit. The septum purge flow channel 12 has a certain flow resistance. Further, the septum purge flow channel 12 has a pressure sensor 20 for detecting the pressure at the proximal end portion of the sample introduction unit. The pressure-regulating system of the carrier gas introduction tube 10 receives a detection output from the pressure sensor 20 to regulate the flow rate of a carrier gas.

The proximal end portion of the sample introduction unit is sealed with a septum 14. A liquid sample is injected into the glass insert 2 by allowing a needle 18 of a syringe of a sample injector 16 to penetrate the septum 14 in such a manner that the distal end of the needle 18 is inserted into the inside of the glass insert 2. The syringe for injecting a sample into the glass insert 2 through the needle 18 is controlled by the sample injector 16 so that a sample can be automatically injected into the glass insert 2.

The sample vaporization unit 4 is, for example, a chip, and has a base frame 22, a flow channel 24 provided in the base frame 22, and a rugged portion 26 provided by microfabrication in the flow channel 24 to vaporize a sample. In order to electrically heat the rugged portion 26, an electrode for connecting the rugged portion 26 to a power supply device 27 is provided.

A through hole 28 is provided on the sample introduction unit side of the flow channel 24 and a through hole 29 is provided on the sample discharge side of the flow channel 24. The through hole 29 is connected to the glass tube 5, and the glass tube 5 has a carrier gas introduction tube 11 and a split flow channel 13 for discharging part of a carrier gas.

The rugged portion 26 is made of at least one material selected from the group consisting of silicon, an inorganic silicon compound, metal, carbon, and ceramic or a complex of two or more of these materials. A method for forming the rugged portion 26, which varies depending on the type of material used, and the shape of the rugged portion 26 will be described later.

Figure 2:
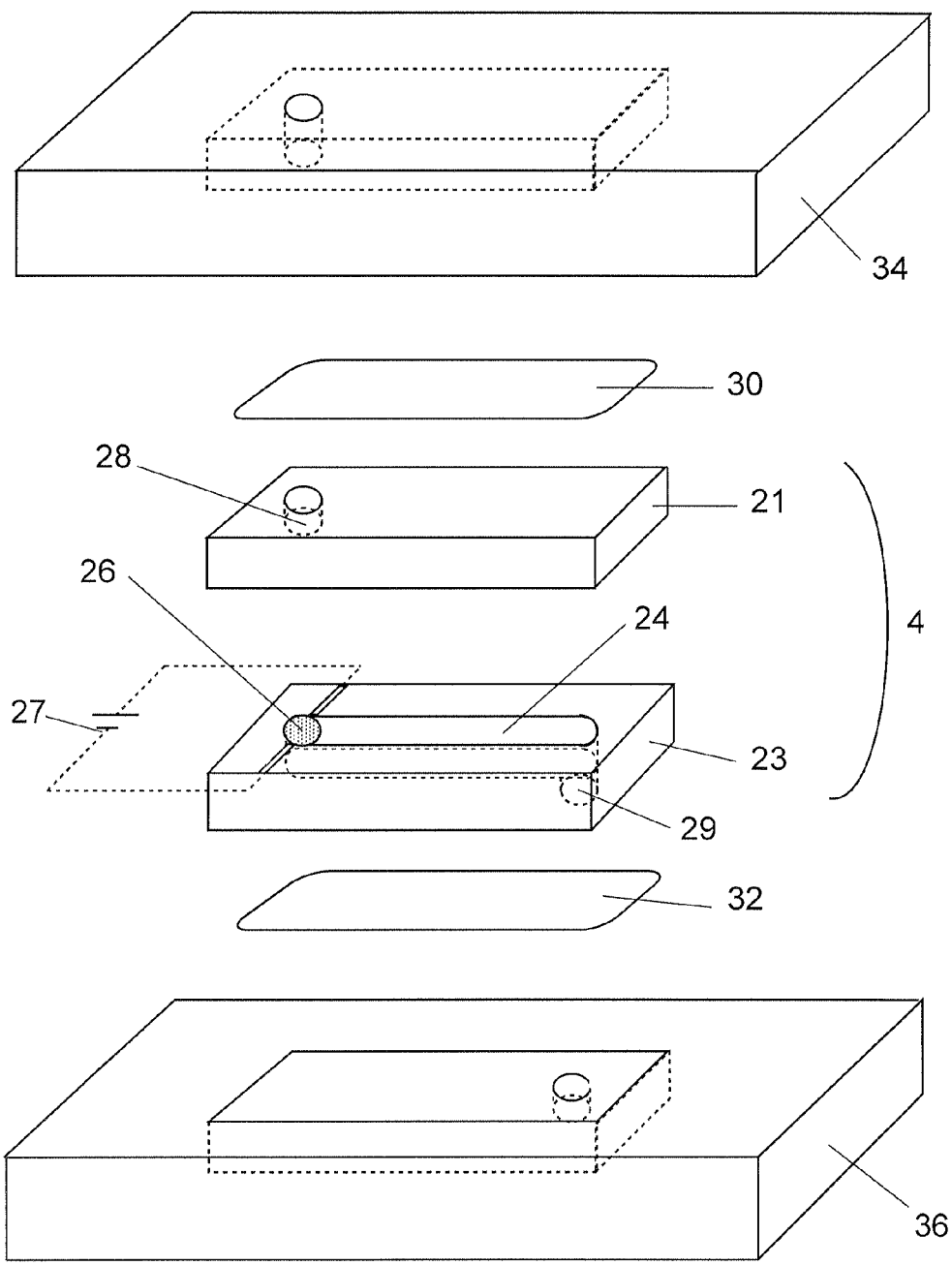
FIG. 2 is an exploded perspective view of a sample vaporization unit of the gas chromatograph according to the first embodiment of the present invention.

FIG. 2 is an exploded perspective view of the sample vaporization unit of the gas chromatograph according to the first embodiment of the present invention.

Reference numeral 21 denotes a glass substrate, and 23 denotes a silicon substrate. The flow channel 24 is provided on one surface of the silicon substrate 23. The through hole 29, which serves as a sample outlet for discharging a sample from the flow channel 24, is also provided in the silicon substrate 23. The through hole 28, which serves as a sample inlet for introducing a sample into the flow channel 24, is provided in the glass substrate 21.

The through hole 28 is located at a position corresponding to the rugged portion 26 provided in the flow channel 24. A gold or platinum electrode formed by, for example, sputtering is provided on the upper surface of the rugged portion 26 and at a position at which the rugged portion 26 is connected to the external power supply device 27.

The substrate 21 and the substrate 23 are bonded together in such a manner that the surface of the substrate 23 having the flow channel 24 is bonded to the substrate 21. The sample vaporization unit 4 obtained by bonding together the substrates 21 and 23 is interposed between a jig 34 and a jig 36 in such a manner that a gasket 30 is provided between the upper surface of the sample vaporization unit 4 and the jig 34 and a gasket 32 is provided between the lower surface of the sample vaporization unit 4 and the jig 36. Alternatively, O-rings may be used as the gaskets 30 and 32.

The size of the sample vaporization unit 4 is not particularly limited, but each of the substrates 21 and 23 preferably has a size of about 20 mm×50 mm, and the flow channel 24 preferably has a width of about 2 mm, a depth of about 0.5 mm, and a length of about 30 mm. The rugged portion 26 preferably has a diameter of about 3 mm.

Hereinbelow, the operation of the gas chromatograph according to the first embodiment of the present invention will be described with reference to FIG. 1.

The temperature of the oven 7 is set to 150° C. to maintain the capillary column 6 at a constant temperature. The power supply device 27 applies an electric current to the rugged portion 26 so that the rugged portion 26 is heated to 250° C.

A carrier gas whose pressure has been regulated to be constant is supplied to the proximal end portion of the sample introduction unit. In this state, a liquid sample of about 1 μL is injected from the sample injector 16 into the glass insert 2 through the needle 18. An excess of the carrier gas to be introduced into the glass insert 2 is discharged to the outside through the septum purge flow channel 12.

The liquid sample is instantly vaporized by heat generated by the rugged portion 26, and is carried by the carrier gas, which flows through the flow channel 24, to the sample discharge side of the flow channel 24, and is then split into two at a split ratio of 200:1 and introduced into both the split flow channel 13 and the capillary column 6. The sample introduced into the column 6, which is maintained at a constant temperature by the oven 7, is separated in the column 6 into its components, and the sample components are detected by the detector 8.

In the case of the gas chromatograph according to the first embodiment of the present invention, a liquid sample is injected from the sample injector 16 into the glass insert 2 through the needle 18. However, sample injection may be carried out by dropping a sample of about 1 μL onto the surface of the rugged portion 26 through a sample injection port with the use of an automatic sampler, an automatic injector, or a microsyringe.

Figure 3:
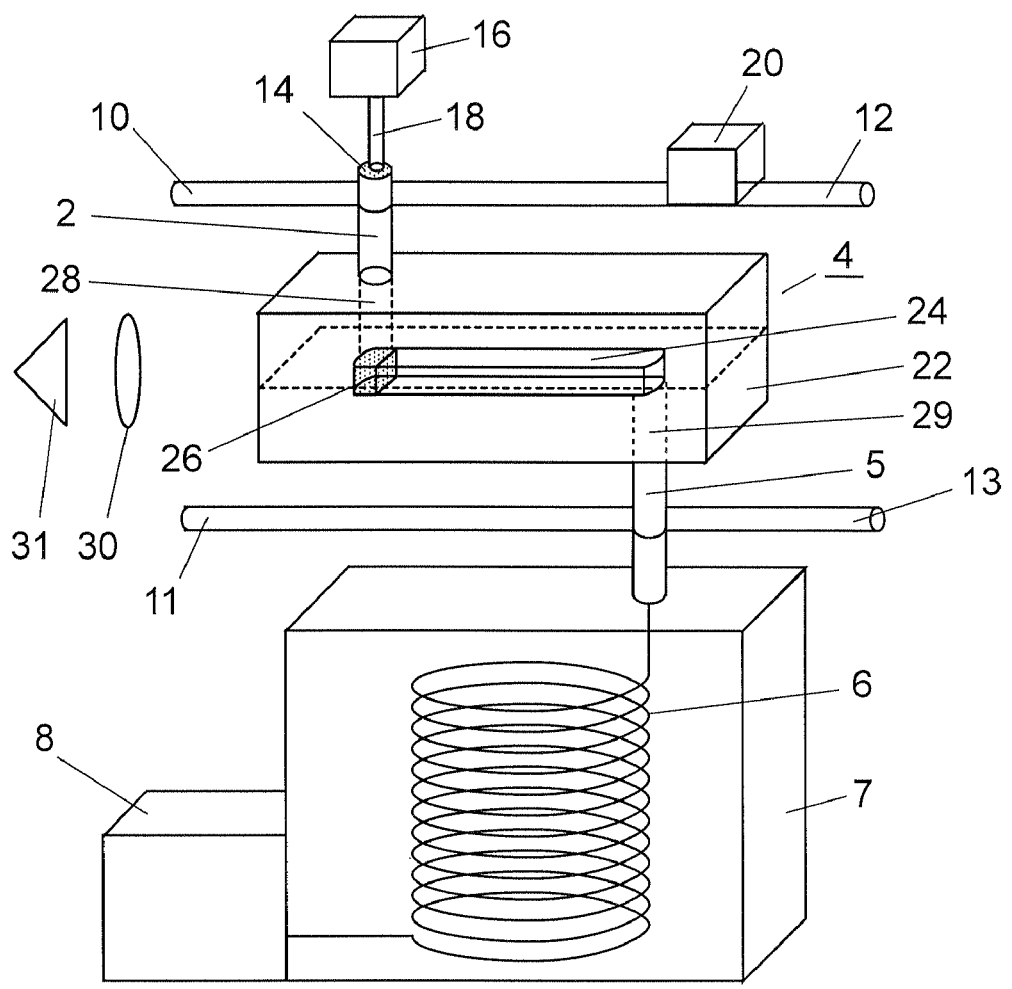
FIG. 3 is a schematic perspective view of a gas chromatograph according to a second embodiment of the present invention.

Hereinbelow, a second embodiment of the present invention will be described with reference to FIG. 3.

A gas chromatograph according to the second embodiment of the present invention has the same device configuration as the gas chromatograph shown in FIG. 1. More specifically, the distal end of the glass insert 2 is connected to one end of the sample vaporization unit 4, the other end of the sample vaporization unit 4 is connected to one end of the capillary column 6 through the glass tube 5, and the other end of the capillary column 6 is led to the detector 8. The glass tube 5 has the carrier gas introduction tube 11 and the split flow channel 13 for discharging part of a carrier gas.

The sample vaporization unit 4 has the base frame 22, the flow channel 24 provided in the base frame 22, and the rugged portion 26 provided by microfabrication in the flow channel 24 to vaporize a sample. The through hole 28 is provided on the sample introduction unit side of the flow channel 24 and the through hole 29 is provided on the sample discharge side of the flow channel 24.

In order to heat the rugged portion 26 by external radiant heat, an energy source 31 and a converging lens 30 for converging energy emitted from the energy source 31 are provided near the sample vaporization unit 4.

Hereinbelow, the operation of the gas chromatograph according to the second embodiment of the present invention will be described.

A liquid sample is injected from the sample injector 16 into the glass insert 2 through the needle 18, and is then introduced into the sample vaporization unit 4 together with a carrier gas introduced through the carrier gas introduction tube 10. The rugged portion 26 provided in the sample vaporization unit 4 is previously heated to 250° C. by radiant heat emitted from the energy source 31, and therefore the liquid sample is vaporized by heat generated by the rugged portion 26.

The vaporized sample is carried by the carrier gas, which flows through the flow channel 24, to the sample discharge side of the flow channel 24, and is then split into two at a split ratio of 200:1 and introduced into both the split flow channel 13 and the capillary column 6. The sample introduced into the column 6, which is maintained at a constant temperature (150° C.) by the oven 7, is separated in the column 6 into its components, and the sample components are detected by the detector 8.

In the case of the gas chromatograph according to the second embodiment of the present invention, laser light such as $N_2$ laser light can be used as energy emitted from the energy source 31 (see Non-Patent Document 1). Particularly, in a case where the rugged portion 26 is made of silicon, YAG laser light or $N_2$ laser light is preferably used.

Further, in the case of the gas chromatograph according to the second embodiment of the present invention, the rugged portion 26 may be heated by electromagnetic induction. In this case, the rugged portion 26 is made of metal and magnetic lines of force are used as an energy source instead of the energy source 31 and the converging lens 30 for converging energy emitted from the energy source 31. The rugged portion 26 is preferably made of iron, stainless steel, or an alloy of them.

Hereinbelow, a method for forming the sample vaporization unit and the rugged portion thereof will be described.

<Method for Forming Rugged Portion 1 (Porous Silicon)>

Figure 4:
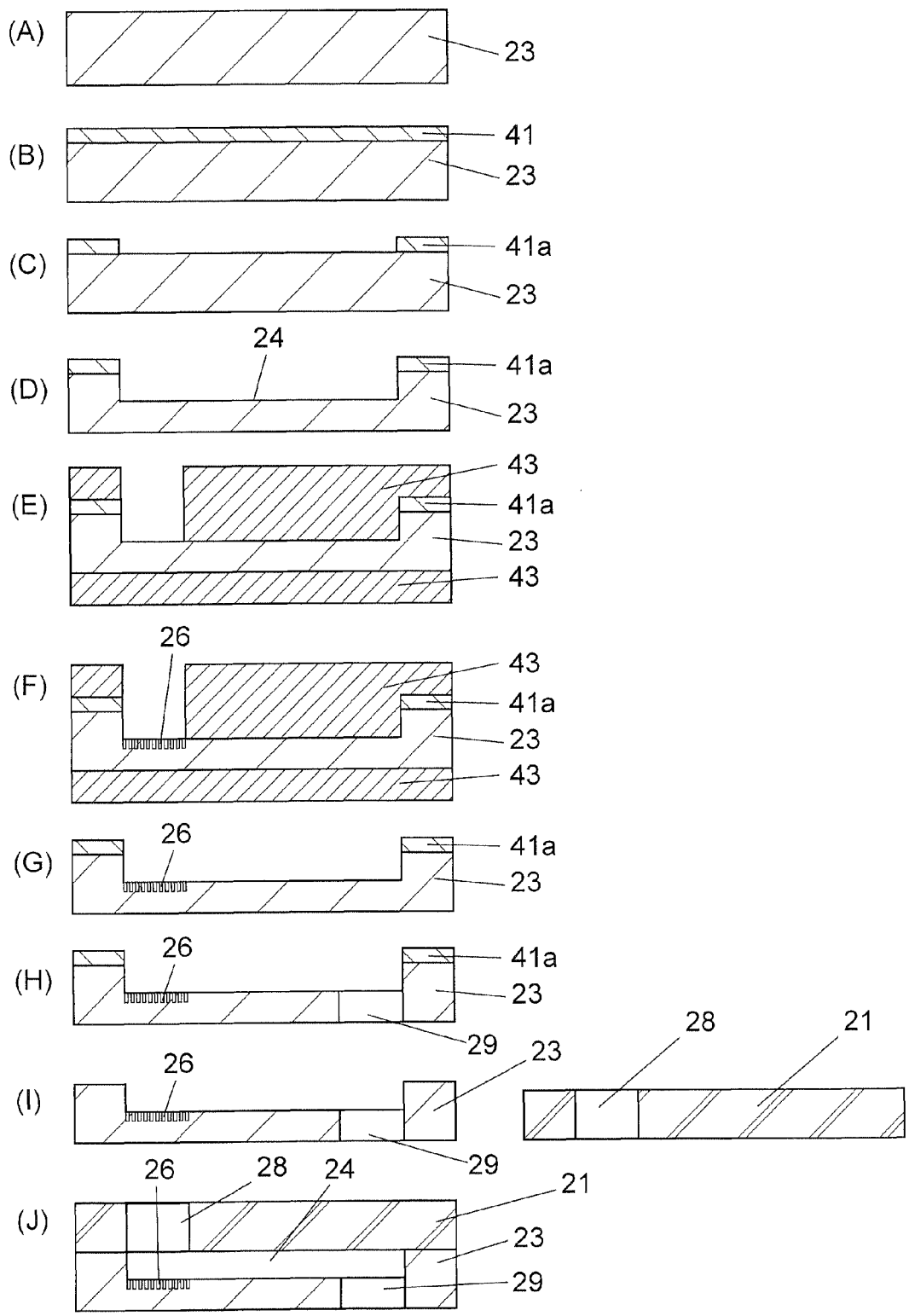
FIG. 4(A) to FIG. 4(J) show a flow chart for explaining one example of the process of forming porous silicon in the sample vaporization unit.

FIG. 4 is a flow chart for explaining the process of forming porous silicon in the sample vaporization unit.

(A) The silicon substrate 23 is prepared.

(B) The upper surface of the silicon substrate 23 is thermally oxidized to form a silicon oxide film 41 on the surface of the silicon substrate 23.

(C) The silicon oxide film 41 is covered with a mask except for an area corresponding to the flow channel 24, and an oxide film pattern 41a is formed on the silicon substrate 23 by photolithography process and etching.

(D) The flow channel 24 is formed on the silicon substrate 23 by ion etching the upper surface of the silicon substrate 23 using the oxide film pattern 41a as a mask.

(E) A photoresist is applied onto the silicon substrate 23 except for an area where the sample vaporization unit 26 should be formed, and a photoresist pattern 43 having an opening corresponding to the area where the sample vaporization unit should be formed is formed by photolithography process.

(F) The silicon substrate 23 is anodized in 20% hydrofluoric acid using the photoresist pattern 43 as a mask to form porous silicon in the area where the sample vaporization unit 26 should be formed (see Non-Patent Document 2).

(G) The photoresist pattern 43 is removed from both surfaces of the substrate 23.

(H) The through hole 29 is formed by ultrasound machining at a position corresponding to a sample outlet for discharging a sample from the flow channel 24. Alternatively, the through hole 29 may be formed by sandblasting.

(I) The silicon oxide film is removed using hydrofluoric acid. It is to be noted that the through hole 28 is previously formed by a process method such as sandblasting in the glass substrate 21 at a position corresponding to the rugged portion 26.

(J) Finally, the glass substrate 21 and the silicon substrate 23 are bonded together by anodic bonding in such a manner that the upper surface of the silicon substrate 23 having the flow channel 24 is bonded to the glass substrate 21. Alternatively, the glass substrate 21 and the silicon substrate 23 having a silicon oxide film formed thereon may be bonded together using hydrofluoric acid.

<Method for Forming Rugged Portion 2 (Porous Silicon)>

Figure 5:
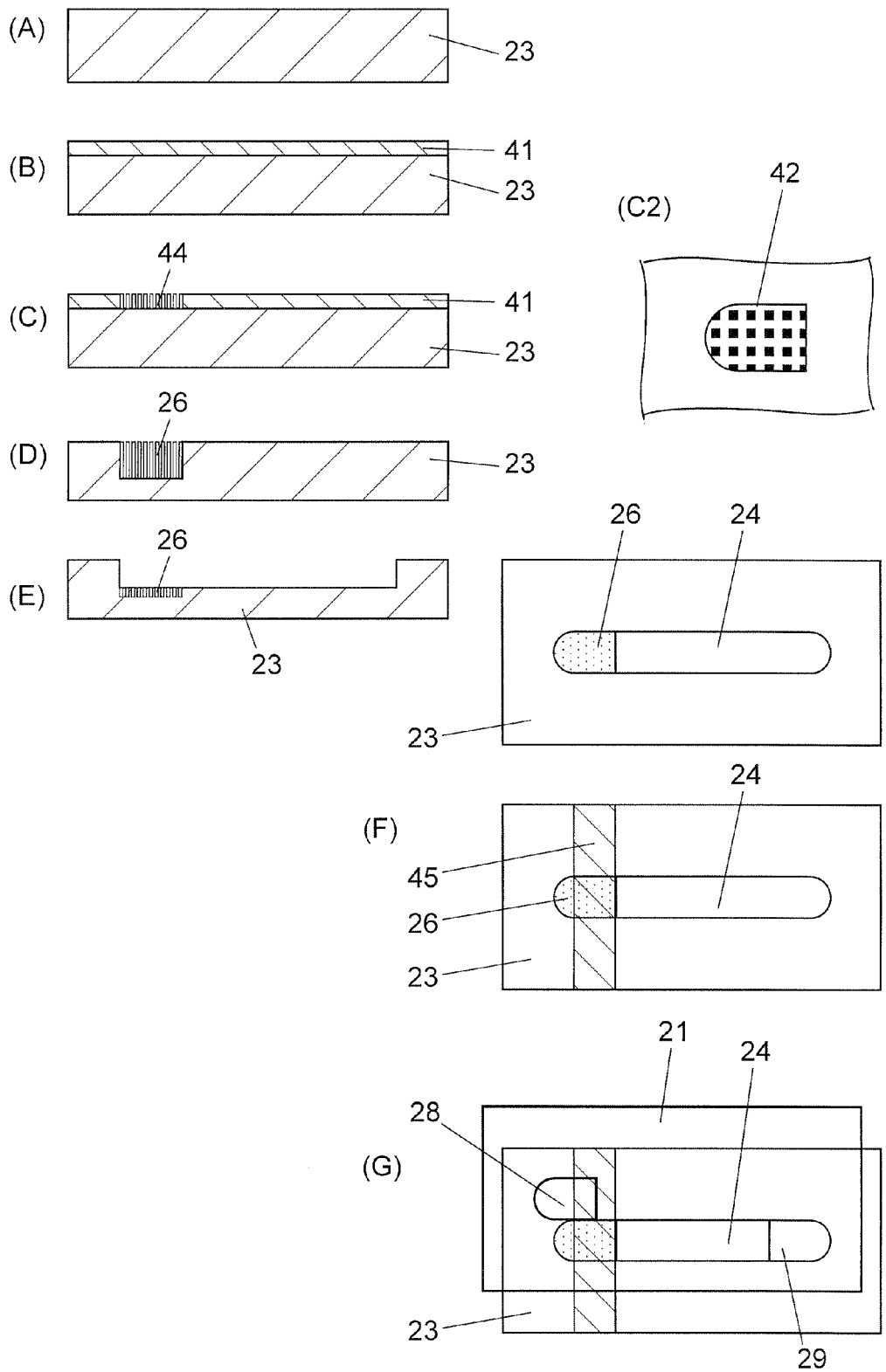
FIG. 5(A) to FIG. 5(G) show a flowchart for explaining another example of the process of forming porous silicon in the sample vaporization unit.

FIG. 5 is another flow chart for explaining the process of forming porous silicon in a chip serving as the sample vaporization unit. It is to be noted that in FIG. 5, views on the left side are sectional views and views on the right side are plan views.

(A) The silicon substrate 23 is prepared.

(B) The upper surface of the silicon substrate 23 is thermally oxidized to form a silicon oxide film 41 on the surface of the silicon substrate 23.

(C) A resist (not shown) is applied onto the silicon oxide film 41 to form a resist pattern by photolithography process using a mask 42 shown in FIG. 5 (C2). The mask 42 has a pattern for forming the sample vaporization unit in the substrate 23, and each black dot in the mask 42 represents a portion where a Cr film is present and an area except for the black dots in the mask 42 allows light to pass through it. Further, the silicon oxide film 41 is etched using the resist pattern as a mask to form a silicon oxide film pattern 44 on the silicon substrate 23.

(D) The silicon substrate 23 is etched by deep ion etching using the silicon oxide film pattern 44 as a mask to form the rugged portion 26 (see Non-Patent Document 3).

(E) The flow channel 24 is formed on the surface of the silicon substrate 23 having the rugged portion 26 by photolithography process and ion etching.

(F) A Ti film and a Pt film are formed on the rugged portion 26 and on the surface of the silicon substrate 23 by sputtering using a mask to provide a 30 nm-thick conductive electrode 45 having the Ti film as a lower layer and the Pt film as an upper layer.

(G) The through hole 29 is formed by sandblasting in the silicone substrate 23 on the sample discharge side of the flow channel 24. The upper surface of the silicon substrate 23 is bonded to the glass substrate 21 having the through hole 28 formed on the sample introduction side of the flow channel 24.

The bonding of the upper surface of the silicone substrate 23 to the glass substrate 21 is carried out using hydrofluoric acid, and therefore a silicon oxide film is formed on the upper surface of the silicon substrate 23 by sputtering before bonding.

The step (G) has been described with reference to a case where bonding between the substrates 21 and 23 is carried out using hydrofluoric acid, but bonding between the substrates 21 and 23 may be carried out by anodic bonding.

<Method for Forming Rugged Portion 3 (Dry Etching)>

The rugged portion 26 may be formed by anisotropic dry etching. For example, needle-shaped projections (black silicon (see Non-Patent Document 5)) can be formed in a silicon substrate by using Black surface methodology (see Non-Patent Document 4).

For example, in a case where a RIE (reactive ion etching) machine is used, black silicon is formed by machining a silicon substrate under conditions where the applied power is 50 W, the etching pressure is 2.7 Pa, the flow rate of $SF_6$ gas is 20 sccm, and the flow rate of $O_2$ gas is 15 ccm. As described in Non-Patent Document 4 or 5, conditions for forming black silicon vary depending on the type of machine used.

<Method for Forming Rugged Portion 4 (Metallic Rugged Portion)>

The rugged portion may be formed by metallic powder injection molding. In this case, the rugged portion made of metal is formed by injection-molding a mixture of metallic powder (e.g., stainless steel, ceramic, iron, titanium, titanium alloy, iron-nickel alloy, tungsten alloy, or a mixture of two or more of them) and a plastic binder and degreasing and sintering an injection-molded product (see Non-Patent Document 6).

The material of the rugged portion 26 is not limited to silicon as long as it can absorb laser light used. For example, in a case where an $N_2$ laser is used as a laser source, Si, an inorganic silicon compound, metal, carbon, ceramic, or a complex of two or more of them can be used as the material of the rugged portion 26, and in a case where a YAG laser is used as a laser source, metal, ceramic, or a complex of two or more of them can be used as the material of the rugged portion 26.

As described above, the sample vaporization unit 4 can be easily formed by bonding together the silicon substrate 23 and the glass substrate 21, but a substrate made of another material, such as a stainless steel substrate, may be used.

For example, in a case where a stainless steel plate is used, a structure serving as the rugged portion (e.g., porous silicon) is installed in the flow channel previously formed in the stainless steel plate.

Figure 6:
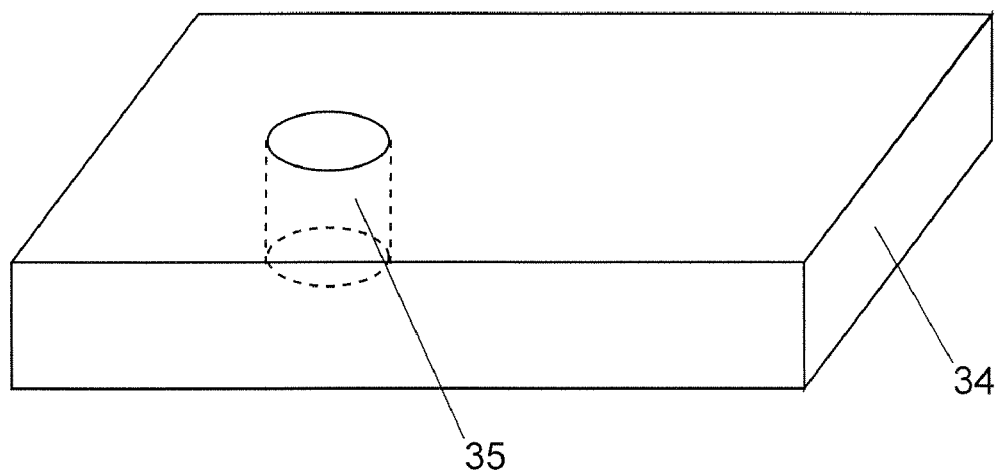
FIG. 6 is a schematic view for explaining a rugged portion formed by machining a stainless steel plate.
Figure 6:
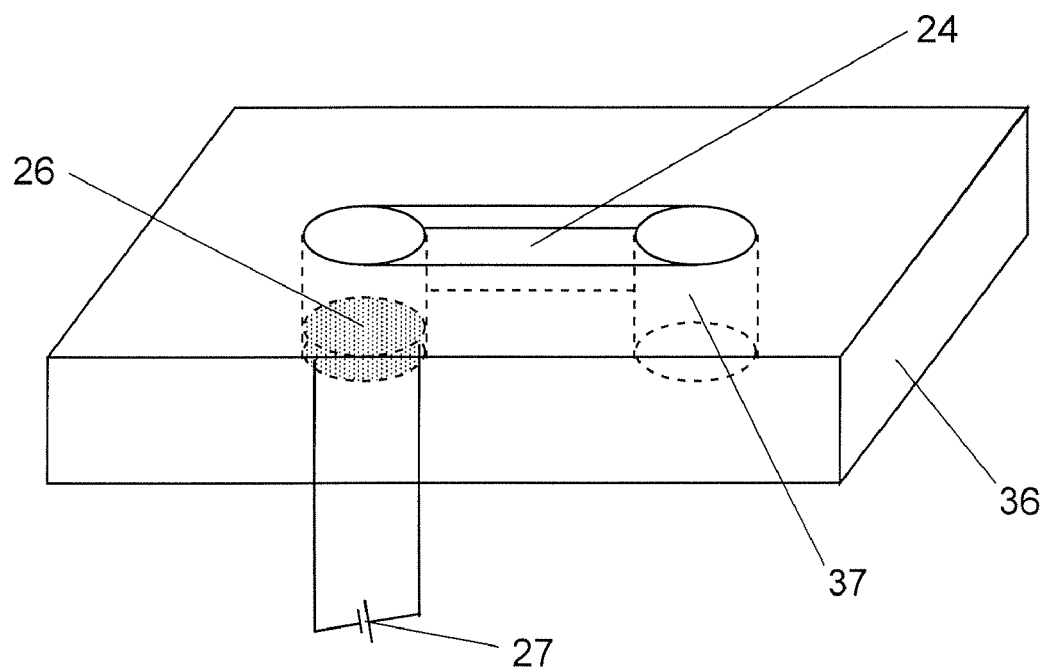
Figure 7:
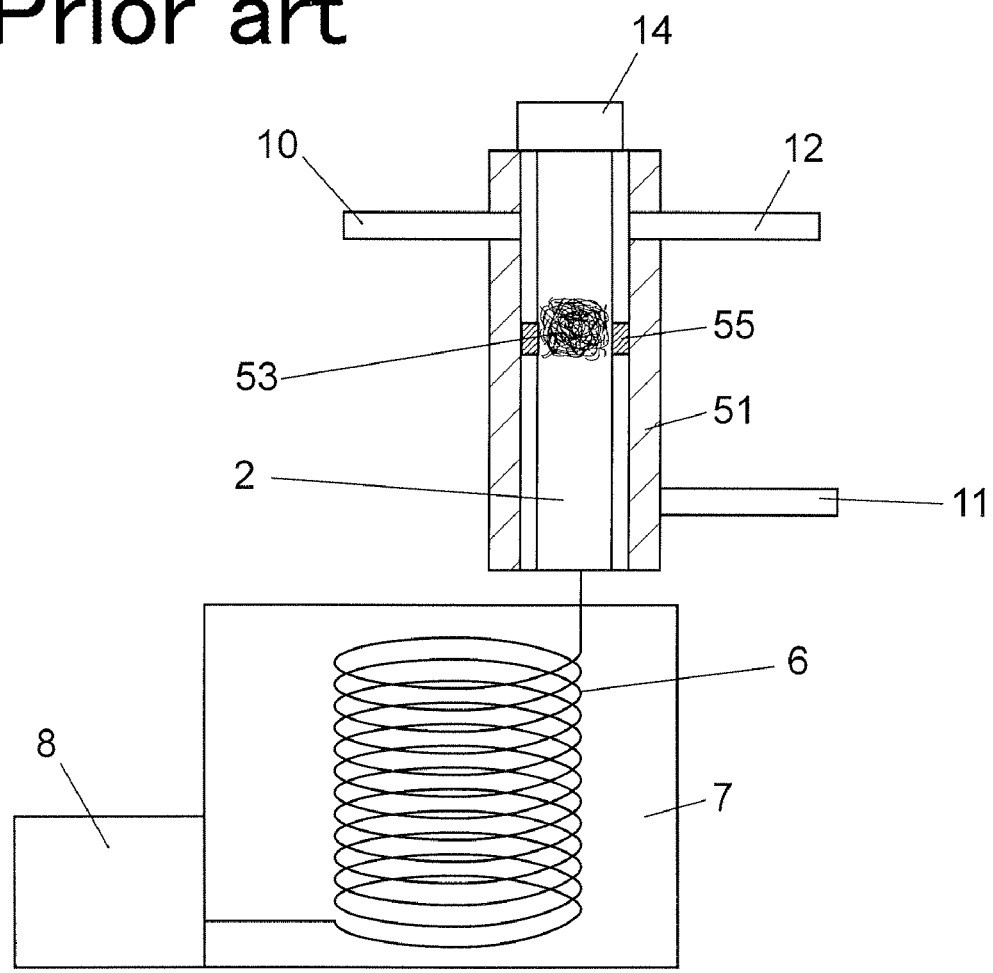
FIG. 7 is a schematic view of a conventional gas chromatograph.

FIG. 6 is a schematic view for explaining a rugged portion formed by machining a stainless steel plate.

A stainless steel jig 34 having a through hole 35 and a stainless steel jig 36 having a through hole 37 and the flow channel 24 are bonded together in such a manner that the flow channel 24 is interposed between the jig 34 and the jig 36. Part of the flow channel 24 is designed as the rugged portion 26, and the rugged portion 26 is connected to the power supply device 27.

The rugged portion 26, the flow channel 24, and the through holes 35 and 37, which are microstructures, can be formed by electro-discharge machining. The jigs 34 and 36 can be bonded together by any one of welding, pressure bonding, brazing and soldering, and bonding using an adhesive.

Alternatively, the rugged portion 26 and the flow channel 24 may be formed by directly machining one stainless steel substrate.

INDUSTRIAL APPLICABILITY

The present invention can be applied to a gas chromatograph in which a liquid sample is vaporized by a sample vaporization unit and then separated into its components to detect the sample components.

What is claimed is:

1. A gas chromatograph comprising:
   a sample vaporization unit having a base frame, a flow channel provided in the base frame, and a rugged portion provided by microfabrication in the flow channel to vaporize a sample;
   an energy supply unit for supplying energy for heating the rugged portion;
   a column connected to the sample vaporization unit to separate the sample carried by a carrier gas from the sample vaporization unit into its components; and
   a detector connected to a discharge side of the column to detect the components of the sample discharged from the column,
   wherein the rugged portion is one selected from the group consisting of
   (A) porous silicon,
   (B) needle-shaped projections being formed by anisotropic dry etching of silicon,
   (C) needle-shaped projections being black silicon, and
   (D) one being formed by injection molding, which has a rectangular cross section or a circular cross section or is constituted from needle-shaped projections.

2. The gas chromatograph according to claim 1, wherein the porous silicon is formed by anodizing silicon in hydrofluoric acid.

3. The gas chromatograph according to claim 1, wherein the pattern having a rectangular cross section is formed by deep ion etching of silicon.

4. The gas chromatograph according to claim 1, wherein the rugged portion is (D) and is made of metal, and
   the energy supply unit has an electrode connected to the rugged portion and a power supply device for supplying an electric current to the rugged portion through the electrode.

5. The gas chromatograph according to claim 1, wherein the energy supply unit is an energy source for supplying radiant energy to the rugged portion.

6. The gas chromatograph according to claim 5, further comprising a lens provided between the energy source and the rugged portion to converge the energy emitted from the energy source.

7. The gas chromatograph according to claim 1, wherein the base frame is formed by bonding together at least two substrates, and wherein the flow channel is formed on at least one of the substrates.

8. The gas chromatograph according to claim 7, wherein one of the substrates is a silicon substrate and the other substrate is a glass substrate.

9. The gas chromatograph according to claim 2, wherein the base frame is formed by bonding together at least two substrates, and wherein the flow channel is formed on at least one of the substrates.

10. The gas chromatograph according to claim 9, wherein one of the substrates is a silicon substrate and the other substrate is a glass substrate.

11. The gas chromatograph according to claim 3, wherein the base frame is formed by bonding together at least two substrates, and wherein the flow channel is formed on at least one of the substrates.

12. The gas chromatograph according to claim 11, wherein one of the substrates is a silicon substrate and the other substrate is a glass substrate.

13. The gas chromatograph according to claim 4, wherein the base frame is formed by bonding together at least two substrates, and wherein the flow channel is formed on at least one of the substrates.

14. The gas chromatograph according to claim 13, wherein one of the substrates is a silicon substrate and the other substrate is a glass substrate.

15. The gas chromatograph according to claim 5, wherein the base frame is formed by bonding together at least two substrates, and wherein the flow channel is formed on at least one of the substrates.

16. The gas chromatograph according to claim 15, wherein one of the substrates is a silicon substrate and the other substrate is a glass substrate.

* * * * *